US007956888B2

(12) United States Patent
Karpen (10) Patent No.: US 7,956,888 B2
(45) Date of Patent: Jun. 7, 2011

(54) REMOTE VIDEO INSPECTION SYSTEM INTEGRATING AUDIO COMMUNICATION FUNCTIONALITY

(75) Inventor: Thomas W. Karpen, Skaneateles, NY (US)

(73) Assignee: GE Inspection Technologies, LP, Schenectady, NY (US)

( * ) Notice: Subject to any disclaimer, the term of this patent is extended or adjusted under 35 U.S.C. 154(b) by 1385 days.

(21) Appl. No.: 11/472,869

(22) Filed: Jun. 22, 2006

(65) Prior Publication Data

US 2007/0070340 A1 Mar. 29, 2007

Related U.S. Application Data

(60) Provisional application No. 60/692,966, filed on Jun. 22, 2005.

(51) Int. Cl.
*H04N 7/18* (2006.01)
(52) U.S. Cl. .......................................................... 348/85
(58) Field of Classification Search .............. 348/82–86
See application file for complete search history.

(56) References Cited

U.S. PATENT DOCUMENTS

| 4,700,693 | A | 10/1987 | Lia et al. |
| 4,727,859 | A | 3/1988 | Lia |
| 4,733,937 | A | 3/1988 | Lia et al. |
| 4,735,501 | A | 4/1988 | Ginsburgh et al. |
| 4,787,369 | A | 11/1988 | Allred, III et al. |
| 4,790,294 | A | 12/1988 | Allred, III et al. |
| 4,794,912 | A | 1/1989 | Lia |
| 4,796,607 | A | 1/1989 | Allred, III et al. |
| 4,853,774 | A | 8/1989 | Danna et al. |
| 4,862,253 | A | 8/1989 | English et al. |
| 4,887,154 | A | 12/1989 | Wawro et al. |
| 4,909,600 | A | 3/1990 | Ciarlei et al. |
| 4,913,369 | A | 4/1990 | Lia et al. |
| 4,941,454 | A | 7/1990 | Wood et al. |
| 4,941,456 | A | 7/1990 | Wood et al. |
| 4,962,751 | A | 10/1990 | Krauter |
| 4,980,763 | A | 12/1990 | Lia |
| 4,989,581 | A | 2/1991 | Tamburrino et al. |
| 4,998,182 | A | 3/1991 | Krauter et al. |
| 4,998,282 | A * | 3/1991 | Shishido et al. ................ 381/77 |
| 5,014,515 | A | 5/1991 | Krauter |
| 5,014,600 | A | 5/1991 | Krauter et al. |
| 5,018,436 | A | 5/1991 | Evangelista et al. |
| 5,018,506 | A | 5/1991 | Danna et al. |
| 5,019,121 | A | 5/1991 | Krauter |

(Continued)

FOREIGN PATENT DOCUMENTS

EP 1512365 3/2005

(Continued)

*Primary Examiner* — Andy S Rao
(74) *Attorney, Agent, or Firm* — Marjama Muldoon Blasiak & Sullivan LLP (57) ABSTRACT

Remote viewing devices and methods are provided to communicate audio information to and/or from a user of the remote viewing device. The audio information can serve an entertainment purpose, and/or can be instructional in order to provide training, guidance and/or feedback to the user prior to or during the inspection process. The audio information can be stored onto physical media such as a CD/DVD disk or a tape, or can be stored as data, such as MP3 data stored within memory accessible to the device. Outputted audio information can be generated by one or more speakers located within the body of the device or located within a headset having a wire line or wireless connection with the remote viewing device.

23 Claims, 8 Drawing Sheets

U.S. PATENT DOCUMENTS

| | | | |
|---|---|---|---|
| 5,047,848 | A | 9/1991 | Krauter |
| 5,052,803 | A | 10/1991 | Krauter |
| 5,061,995 | A | 10/1991 | Lia et al. |
| 5,066,122 | A | 11/1991 | Krauter |
| 5,070,401 | A | 12/1991 | Salvati et al. |
| 5,114,636 | A | 5/1992 | Evangelista et al. |
| 5,140,975 | A | 8/1992 | Krauter |
| 5,191,879 | A | 3/1993 | Krauter |
| 5,202,758 | A | 4/1993 | Tamburrino |
| 5,203,319 | A | 4/1993 | Danna et al. |
| 5,230,059 | A | 7/1993 | Nielsen et al. |
| 5,275,152 | A | 1/1994 | Krauter et al. |
| 5,278,642 | A | 1/1994 | Danna et al. |
| 5,314,070 | A | 5/1994 | Ciarlei |
| 5,323,899 | A | 6/1994 | Strom et al. |
| 5,345,339 | A | 9/1994 | Knieriem et al. |
| 5,347,989 | A | 9/1994 | Monroe et al. |
| 5,365,331 | A | 11/1994 | Tamburrino et al. |
| 5,373,317 | A | 12/1994 | Salvati et al. |
| D358,471 | S | 5/1995 | Cope et al. |
| 5,435,296 | A | 7/1995 | Vivenzio et al. |
| 5,633,675 | A | 5/1997 | Danna et al. |
| 5,701,155 | A | 12/1997 | Wood et al. |
| 5,734,418 | A | 3/1998 | Danna |
| 5,754,313 | A | 5/1998 | Pelchy et al. |
| 5,857,963 | A | 1/1999 | Pelchy et al. |
| 5,894,322 | A | 4/1999 | Hamano et al. |
| 5,911,036 | A | 6/1999 | Wright et al. |
| 6,083,152 | A | 7/2000 | Strong |
| 6,097,848 | A | 8/2000 | Salvati |
| 6,154,560 | A | 11/2000 | Cothren et al. |
| 6,468,201 | B1 | 10/2002 | Burdick |
| 6,483,535 | B1 | 11/2002 | Tamburrino et al. |
| 6,494,739 | B1 | 12/2002 | Vivenzio et al. |
| 6,524,237 | B1 | 2/2003 | McGowan |
| 6,538,732 | B1 | 3/2003 | Drost et al. |
| 6,545,704 | B1 * | 4/2003 | Olsson et al. .................. 348/84 |
| 6,590,470 | B1 | 7/2003 | Burdick |
| 6,652,451 | B2 | 11/2003 | Murata et al. |
| 6,772,098 | B1 | 8/2004 | Stark et al. |
| 6,830,545 | B2 | 12/2004 | Bendall |
| 6,950,829 | B2 | 9/2005 | Schlabach et al. |
| 6,953,432 | B2 | 10/2005 | Schiefer |
| 7,134,993 | B2 | 11/2006 | Lia et al. |
| 7,170,677 | B1 | 1/2007 | Bendall et al. |
| 7,391,433 | B2 * | 6/2008 | Pollack .......................... 348/85 |
| 7,422,559 | B2 * | 9/2008 | Kehoskie et al. .............. 600/140 |
| 7,551,197 | B2 * | 6/2009 | Penza et al. ..................... 348/84 |
| 7,705,878 | B2 * | 4/2010 | Mandal et al. ................... 348/85 |
| 2002/0128790 | A1 | 9/2002 | Woodmansee |
| 2002/0172498 | A1 | 11/2002 | Esenyan et al. |
| 2003/0055410 | A1 | 3/2003 | Evans et al. |
| 2003/0068057 | A1 | 4/2003 | Miller et al. |
| 2003/0097042 | A1 | 5/2003 | Eino |
| 2003/0105565 | A1 | 6/2003 | Loda et al. |
| 2003/0120517 | A1 | 6/2003 | Eida et al. |
| 2003/0128400 | A1 | 7/2003 | Watai et al. |
| 2003/0139671 | A1 | 7/2003 | Walston et al. |
| 2003/0215128 | A1 | 11/2003 | Thompson |
| 2003/0216715 | A1 | 11/2003 | Moll et al. |
| 2003/0236446 | A1 | 12/2003 | Eino |
| 2004/0015778 | A1 | 1/2004 | Britton et al. |
| 2004/0019255 | A1 | 1/2004 | Sakiyama |
| 2004/0054278 | A1 | 3/2004 | Kimchy et al. |
| 2004/0073455 | A1 | 4/2004 | McConnochie et al. |
| 2004/0183900 | A1 | 9/2004 | Karpen et al. |
| 2004/0215413 | A1 | 10/2004 | Weldum et al. |
| 2005/0009397 | A1 | 1/2005 | Takeda et al. |
| 2005/0015480 | A1 | 1/2005 | Foran |
| 2005/0050707 | A1 | 3/2005 | Scott et al. |
| 2005/0093974 | A1 | 5/2005 | Hibi et al. |
| 2005/0129108 | A1 | 6/2005 | Bendall et al. |
| 2005/0162643 | A1 | 7/2005 | Karpen |
| 2005/0165275 | A1 | 7/2005 | Von Felten et al. |
| 2005/0177023 | A1 | 8/2005 | Abe |
| 2005/0187739 | A1 | 8/2005 | Baust et al. |
| 2005/0200698 | A1 | 9/2005 | Amling et al. |
| 2005/0281520 | A1 | 12/2005 | Kehoskie et al. |
| 2006/0050983 | A1 | 3/2006 | Bendall et al. |
| 2006/0072903 | A1 | 4/2006 | Weldum et al. |

FOREIGN PATENT DOCUMENTS

| | | | |
|---|---|---|---|
| WO | WO 2004/025963 | 3/2004 | |

* cited by examiner

REMOTE VIDEO INSPECTION SYSTEM INTEGRATING AUDIO COMMUNICATION FUNCTIONALITY

CROSS-REFERENCE TO RELATED APPLICATIONS

This application claims priority to, the benefit of, and incorporates by reference the entirety of U.S. Provisional Patent Application Ser. No. 60/692,966, which was filed on Jun. 22, 2005, U.S. Provisional Patent Application Ser. No. 60/786,829, which was filed on Mar. 27, 2006, and co-pending U.S. patent application Ser. No. 10/768,761, which was filed on Jan. 29, 2004.

FIELD OF THE INVENTION

This invention relates generally to a remote viewing device, and in particular to an audio-compatible remote viewing device that can communicate audio information to a user of the remote viewing device (e.g., for entertainment and/or instructional purposes) and/or from a user of the remote viewing device (e.g., to memorialize observations made during use of the remote viewing device).

BACKGROUND OF THE INVENTION

Due to their design and capabilities, remote viewing devices, and, in particular, borescopes, are often used to search for and inspect defects that may be hidden within difficult to access spaces. For example, it is known to use a remote viewing device to inspect the many heat exchange tubes within a steam generator of a nuclear power plant, or to inspect numerous individual portions of aircraft engines.

When properly performed, inspection processes such as these can entail many hours of solitary effort, and, in turn, can cause the inspector to become bored or inattentive and thus to miss important details revealed during the inspection process. A potential solution to this problem is to provide non-distracting entertainment (e.g., broadcast radio) to an inspector. Unfortunately, remote viewing devices such as borescopes are often used in environments in which it is impossible or logistically impractical to obtain a broadcast radio signal. For example, nuclear power plants are generally surrounded by a containment structure that can interfere with radio reception inside the containment structure. Moreover, places in which airplanes are stored can be quite loud, even loud enough to drown out a broadcast radio signal.

Additionally, those who operate remote viewing devices presently use either a tape recorder and/or a paper and a writing utensil not only to memorialize observations they make during the inspection process but also to receive various instructions related to the inspection process (e.g., how to use the remote viewing device and or some of its features, what potions of an object they are to inspect, etc.). This is not ideal because it requires the inspector to discontinue the inspection process in order to use his hands to obtain or to provide the necessary information. That, in turn, lengthens the duration of the process and, perhaps more significantly, could cause the inspector to forget at what stage he or she was within the overall inspection process, leading to errors.

Thus, there is a need for a remote viewing device that is adapted to provide entertainment and information to, and/or to memorialize observations made by, a user thereof in a manner that causes little to no disruption to the inspection process and that does not inhibit or otherwise negatively affect the usage, operation and functioning of the remote viewing device.

SUMMARY OF THE INVENTION

These and other needs are met by an inspection device, which, in one exemplary aspect, comprises (a) an insertion tube, (b) a control module that is disposed at a proximal end of the insertion tube, (c) a viewing head that is in electrical and optical communication with the control module through the insertion tube, and an audio information manipulation system. The audio information manipulation system is adapted to communicate audio information to a user of the inspection device, wherein such audio information can include, but is not limited to, menu-driven inspection information; error notification information, feedback information and audio entertainment information.

In accordance with this and other aspects of the inspection device, the audio information pertaining to the menu-driven inspection can be communicated to said user upon said user highlighting a menu option, browsing within menu options, and/or selecting a menu option. The audio information can be communicated to the user via, for example, one or more one speakers (e.g., stereo speakers or surround sound speakers) that are in communication (e.g., via a wireless or wire line connection) with said audio information manipulation system. The one or more speakers can be disposed outside of the inspection device, such as within a headset in communication with the audio information manipulation system. The headset can be in communication with the audio information manipulation system via a wire line or wireless connection.

Such needs also can be met through use of a remote viewing device that comprises: (a) an insertion tube that has a proximal and a distal end, (b) a control module that is disposed at the proximal end of the insertion tube, wherein the control module provides at least a first portion of a user interface to a user of the remote viewing device, (c) a viewing head that is disposed at the distal end of the insertion tube, wherein the viewing head inputs and communicates image information to the control module, and (d) at least one audio output device that is configured to communicate audio information to a user of the remote viewing device, wherein audio information is provided to the at least one audio output device to process, and wherein the audio output device is controlled so as to initiate processing and communication of the audio information with the user of the remote viewing device, wherein said audio information is communicated with said user in the form of at least one of audio entertainment information, audio guidance information, audio training information, and audio feedback information.

In accordance with this and other exemplary aspects, the remote viewing device can include additional components, such as a base module that is configured to relay power to at least one other portion of said remote viewing device; a data communications port for receiving audio information stored within digital memory; and/or a user interface adapted to control the at least one audio output device. The data communications port, if present, can provide, e.g., a wireless connection with another computing device. The user interface, if present, can be disposed within the remote viewing device, such as, by way of non-limiting example, within a body portion thereof, within a remote control in communication with the remote viewing device, or within the control module.

Also in accordance with this and other exemplary aspects, the audio information can be processed from one more portable media sources as the audio output device. By way of non-limiting example, such portable media sources can be of a disk player device (e.g., a CD player, a DVD player, a mini disk player) and a tape player device (e.g., a cassette tape player, a videotape player). Moreover, the audio output device can include at least one radio receiver, which can be, by way of non-limiting example, a broadcast radio receiver, a satellite radio receiver, and/or a high definition radio receiver.

Still other aspects, embodiments and advantages of these exemplary aspects are discussed in detail below. Moreover, it is to be understood that both the foregoing general description and the following detailed description are merely illustrative examples of various embodiments, and are intended to provide an overview or framework for understanding the nature and character of the claimed embodiments. The accompanying drawings are included to provide a further understanding of the various embodiments, and are incorporated in and constitute a part of this specification. The drawings, together with the description, serve to explain the principles and operations of the described and claimed embodiments.

BRIEF DESCRIPTION OF THE DRAWINGS

For a fuller understanding of the nature and desired objects of the present invention, reference is made to the following detailed description taken in conjunction with the accompanying figures, wherein like reference characters denote corresponding parts throughout the views, and in which.

DETAILED DESCRIPTION OF THE INVENTION

A remote viewing device, such as an endoscope or a borescope, is generally characterized as an elongated insertion tube with a viewing head at its forward (i.e., distal) end, and a control section at its rear (i.e., proximal) end. The control section enables a user to position and control operation of the viewing head, which generally includes an image sensor and an illumination component that are typically disposed adjacent to each other (i.e., side by side). The viewing head captures and transmits image information from the environment surrounding the distal end of the insertion tube to the control section at the proximal end of the insertion tube for display on a video screen and viewing by a user.

The term "endoscope" generally refers to (and is used herein with reference to) remote viewing devices for remotely inspecting the interior portions of a body cavity for the purpose of medical diagnosis or treatment. The term "borescope" or "industrial endoscope" generally refers to (and is used herein with reference to) remote viewing devices for inspection of interior portions of industrial equipment.

Figure 1A:
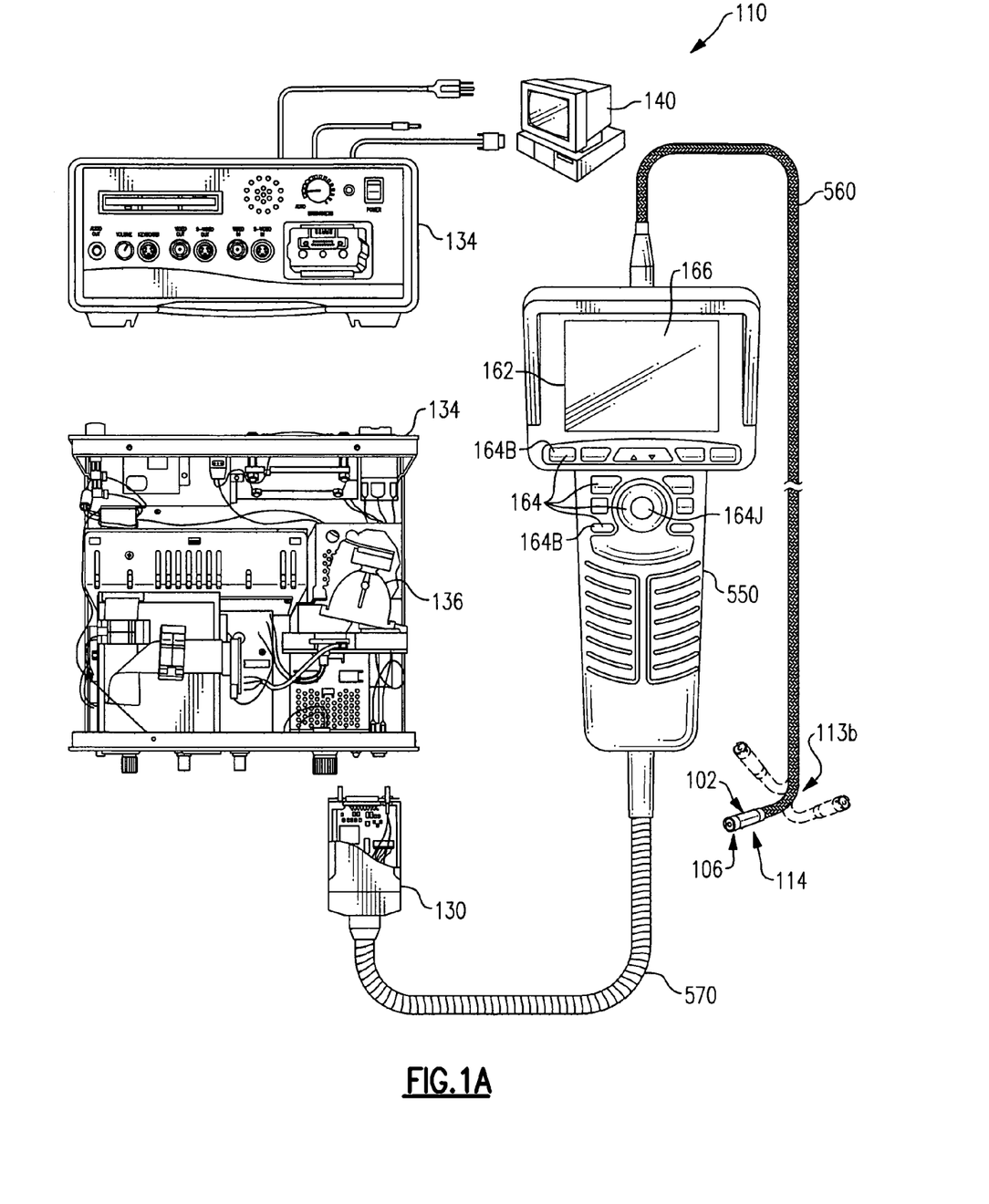
FIGS. 1A-1F illustrate an exemplary embodiment of a remote viewing device including a base module, an umbilical cord, a handset, and an insertion tube.

FIG. 1A illustrates an exemplary embodiment of an insertion tube remote viewing device in accordance with the invention. As shown, the insertion tube remote viewing device 110 includes a base module 134 (also referred to herein interchangeably as a light box), a power plug 130, an umbilical cord 570; a hand set 550 (also referred to herein interchangeably as a hand piece 550), an insertion tube 560 and a viewing head assembly 114.

A light source 136 can be disposed within the light box 134, wherein the light box generally should be capable of directing light through the umbilical cord 570, through the hand set 550, through the insertion tube 560 and outwardly through the viewing head assembly 114 to the surrounding environment. To that end, the light source 136 can be, by way of non-limiting example, a 50-Watt metal halide arc lamp. Alternatively, a light source can be located within other parts of the remote viewing device, such as, by way of non-limiting example, within either the handset 550 or the viewing head assembly 114.

The umbilical cord 570 and the insertion tube 560 enclose fiber optic illumination bundles through which light travels. If desired, the insertion tube 560 also can include an articulation cable 146 (see FIG. 1E) that enables an operator of the remote viewing device 110 to control the movement (i.e., bending) of the insertion tube 560 at its distal end 113b. Alternatively, yet still in accordance with this and other embodiments, other insertion tubes of various designs can be used within the remote viewing device.

As shown in the Figures, the viewing head assembly 114 includes a viewing head 102 and a detachable optical tip 106. Alternatively, the optical tip 106 instead may be configured to be permanently attached, and thus not detachable from the viewing head 102. The viewing head assembly 114 also includes a canister 144 (see FIGS. 1B and 1C) that surrounds an image sensor 312 (see FIG. 1C) and a lens 313 (see FIG. 1C) and that directs and focuses incoming light towards the image sensor 312. Alternatively, yet still in accordance with this and other embodiments, other viewing head assemblies of various designs can be incorporated within the remote viewing device.

The detachable optical tip 106 is formed from a material capable of projecting outgoing light, wherein suitable such materials include but are not limited to a translucent material such as a glass, a plastic light conductor, or a fiber optic illumination bundle. The detachable optical tip 106 also includes a lens 315 for receiving incoming light from the surrounding environment. Generally, but not necessarily, the detachable optical tip 106 includes one or more a light sources, such as, by way of non-limiting example, one or more light emitting diodes (LEDs) that project light to the surrounding environment. If desired, the detachable optical tip 106 can be replaced by other detachable optical tips 106 with differing operational characteristics, such as with differing illumination characteristics and/or differing light re-direction and/or light focusing and/or field/depth of view characteristics.

In an exemplary embodiment, an image processing circuit (not shown), residing within the light box 134, processes image information received by and communicated from the viewing head 114 to the light box 134. A purpose of the image processing circuit, if included, is to correct non-uniformities in a captured frame of image data that are attributable to non-uniformities of the illumination pattern projected by the optical tip 106 of the device 110.

A continuous video image is displayed via the hand set display 162 and/or the monitor display 140. The hand set 550, also referred to herein interchangeably as a handset, receives user command inputs via hand set controls 164 in order to perform various remote insertion tube device operations. A hand set control circuit (not shown) interprets user commands via hand set controls 164 so as to move the distal end 113b of the insertion tube 560 into a desired orientation. Hand set controls 164 can include, but are not limited to various control buttons 164B and a joystick 164J. If desired, and in lieu of or in addition to the control buttons 164B and/or joystick 164J, the hand set controls 164 can include a means to enter graphical user interface (GUI) commands.

In an exemplary embodiment, the image processing circuit and hand set control circuit are microprocessor based and utilize one or a plurality of readily available programmable off-the-shelf microprocessor integrated circuit (IC) chips. Microprocessor IC chips have on-board volatile and nonvolatile memory that store and that execute programming logic and are optionally in communication with external volatile and nonvolatile memory devices.

The interior of the base unit (light box) 134 is substantially displaced by various electrical components in order to support the operation of the remote viewing device 110. In addition to housing the image processing circuit, the base unit 134 and power plug 130 also carry various electrical circuitries for delivering electrical power to various components of the device 110.

Figures 1B, 1C, 1D, 1E, 1F:
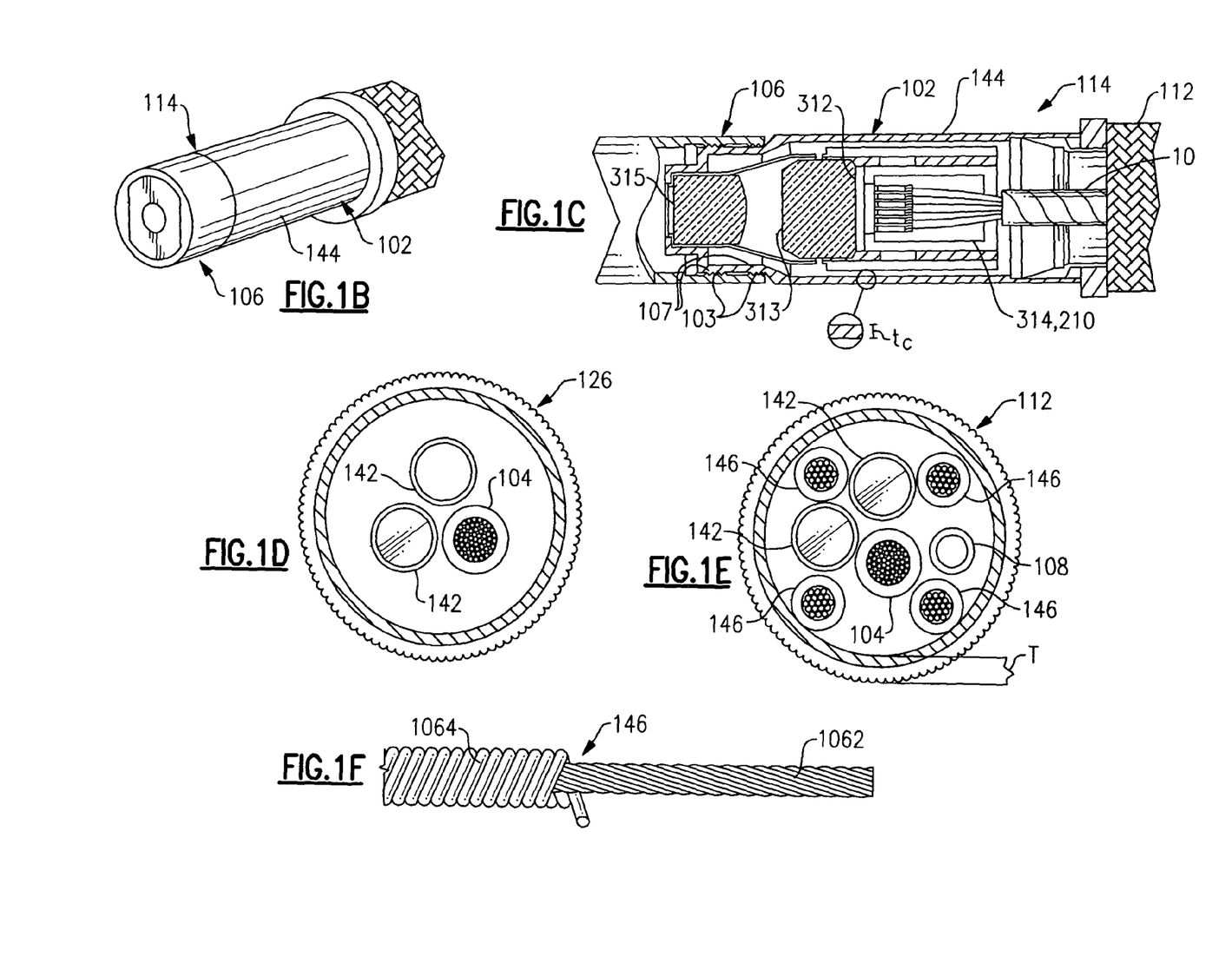

FIG. 1B illustrates an exemplary embodiment of a viewing head assembly 114 that includes a viewing head 102 and a detachable optical tip 106 like that illustrated in FIG. 1A. The viewing head 102 includes a metal canister 144 which encapsulates a lens (see FIG. 1C) and an image sensor 312 (see FIG. 1C) as well as elements of an image signal conditioning circuit 210. By way of non-limiting example, the viewing head 102 and optical tip 06 may include respective threads 103 and 107, which enable optical tip 106 to be attached and detached as desired to the viewing head 102. It is understood, however, that other known fasteners providing detachable attachment of the tip 106 to the viewing head 114 may be substituted for threads 103 and 107.

FIG. 1C illustrates a cross-sectional view of the exemplary embodiment of the viewing head assembly 114 of FIG. 1B, including the viewing head 102 and the detachable optical tip 106 like that illustrated in FIGS. 1A and 2B. Alternatively, yet still in accordance with this and other embodiments, other viewing heads of various designs can be used to support the operation of the remote viewing device.

As shown for this type of exemplary embodiment, the optical tip 106 includes a lens 315 and threads 103 along an inner surface. The viewing head 102 includes a lens 313 and threads 107 along an outer surface. The threads 103 of the optical tip 106 can be engaged with the threads 107 of the viewing head 102 so as to attach the optical tip 106 to the viewing head 102. When the optical tip 106 is attached to the viewing head 102 as such, the lens 315 of the optical tip 106 is disposed and aligned in series with the lens 313 of the viewing head 102.

The viewing head 102 of the device 110 is encapsulated by a metal canister 144 which, in turn, encapsulates the lens 313, an image sensor 312 and an imager component circuit 314. The imager component circuit 314 includes an image signal conditioning circuit 210 and is attached to a wiring cable bundle 104 that extends through the insertion tube 560 to connect the viewing head 102 to the handset 550 (see FIG. 1A). In this exemplary embodiment, a wiring cable bundle passes through the hand set 550 and the umbilical cord 570 to the power plug 130.

FIG. 1D illustrates a cross-sectional view of the umbilical cord 570, which, as shown, encases the light conducting fiber optic bundles 142. The umbilical cord 570 further encases a wiring cable bundle 104 that includes a plurality of wires. A first subset of the plurality of wires of wiring cable bundle 104 are terminated within hand set 550 and do not extend through the insertion tube 560. A remaining second subset of the wires of the wiring cable bundle 104 are not terminated within hand set 550, and thus extend through the insertion tube 560. Alternatively, yet still in accordance with this and other embodiments, other umbilical cords of various designs can be used to support the operation of the remote viewing device.

FIG. 1E illustrates a cross-sectional view of the insertion tube 560. The insertion tube 560 encases light conducting fiber optic bundles 142, the wiring cable bundle 104, articulation cable assemblies 146, and a working channel 108. The working channel 108 allows manipulation of a tool (e.g., a hook, a brush, or a magnet) extending from viewing head assembly 114. Alternatively, other viewing heads of various designs can be used to support the operation of the remote viewing device. The articulation cable assemblies 146 enable bending of insertion tube 560 at its distal end 113b. As best shown in FIG. 1F, the articulation cable assemblies 146 are provided by a stranded cable 1062 encased by an outer spring conduit 1064. Alternatively, yet still in accordance with this and other embodiments, other insertion tubes of various designs can be used to support the operation of the remote viewing device.

Figure 1G:
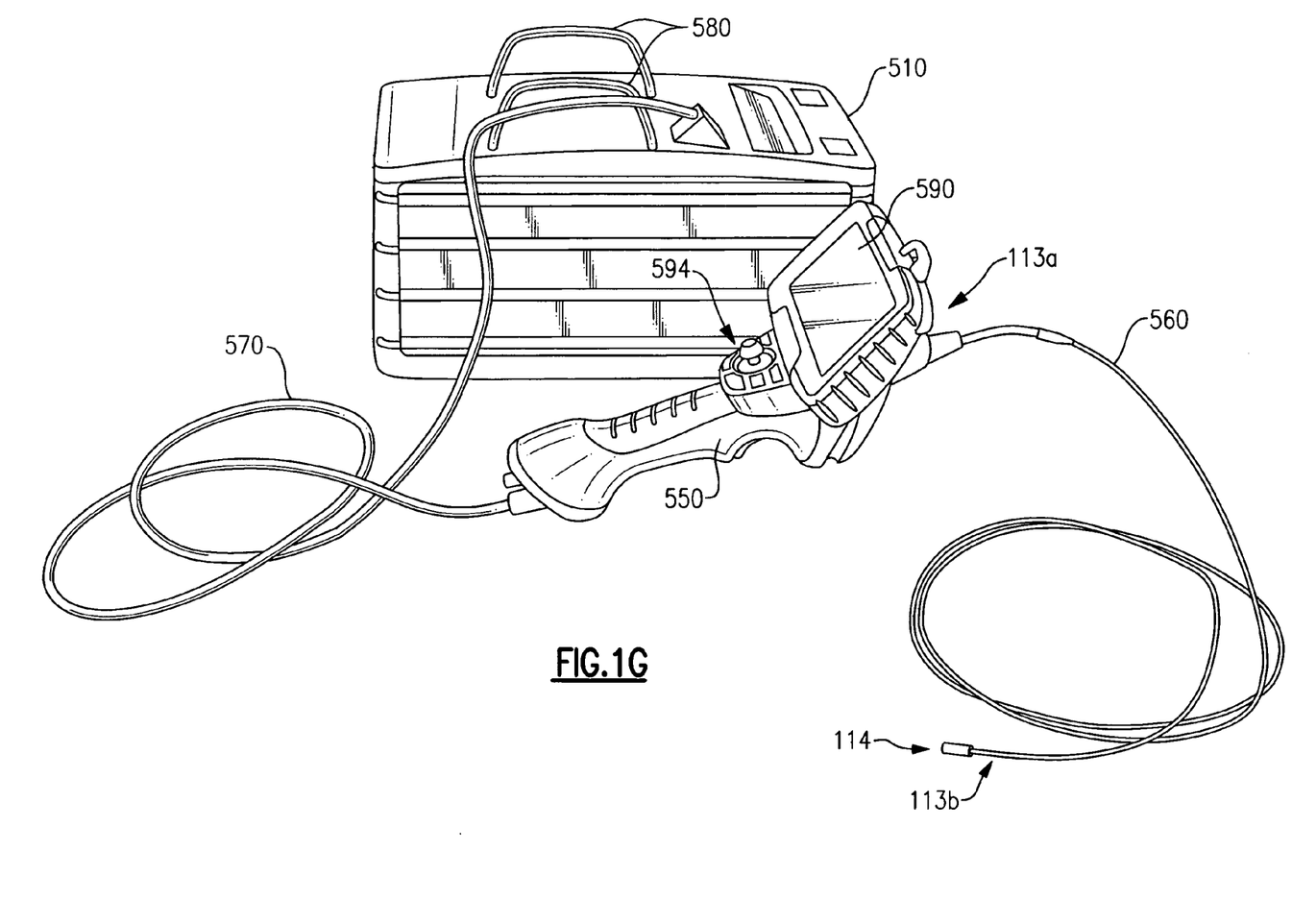
FIG. 1G illustrates another exemplary embodiment of a remote viewing device including an alternate portable base module, an umbilical cord, a handset, and an insertion tube.

FIG. 1G illustrates another exemplary embodiment of a remote viewing device 110 showing an alternate embodiment of the base module 510 wherein the base module 510 is connected by an umbilical cord 570 to a handset 550, which, in turn, is connected to an insertion tube 560. The insertion tube 560 has a proximal end 113a and a distal end 113b and a viewing head assembly 114 attached to its distal end.

The base module 510 is electronically and optically connected to the handset 550 via the umbilical cord 570. The handset 550 functions as a control module and is electronically and optically connected to a viewing head assembly 114 via the insertion tube 560. The umbilical cord 570 and the insertion tube 560 enclose fiber optic illumination bundles through which light travels. If desired, the insertion tube 560 also can carry an articulation cable that enables the user to control the orientation (i.e., bending) of the distal end 113b of the insertion tube 560 and the attached viewing assembly 114.

The base module 510 includes a light source module (not shown), which generates light that travels through the umbilical cord 570, through the handset 550, through the insertion tube 560 and outwardly through the viewing head assembly 114. Alternatively, yet still in accordance with this and other embodiments, a light source can be located within other parts of the remote viewing device, for example, a light source can be located within the handset 550 or the viewing head assembly 114.

In use, the viewing head 114 is positioned and oriented to project light towards, and to receive light from a target of interest located within a difficult to access space. Handles 580 can be provided as a means for facilitating the carrying of the base module 510. In included, the handles 580 can be foldable and/or demountable from the base module 510.

The light source module comprises an illumination lamp, such as a xenon arc lamp, which can be, by way of non-limiting example, a 50-Watt metal halide arc lamp. A continuous video image is captured by the viewing head assembly 114 and is displayed via the handset display 590 and/or the monitor display (not shown). The handset 550 also receives command input from a user via the handset controls 594 in order to perform various remote insertion tube device 560 operations. Various designs of handset controls 594, including but not limited to the handset controls 164 described in FIG. 1A, can be employed to support the operation of the remote viewing device 114.

A handset control circuit (not shown) that is disposed within the handset 550 interprets commands entered via handset controls 594 so that the distal end 113b of insertion tube 560 can be moved into a desired orientation. The handset controls 594 can include one or more buttons and/or knobs (e.g., turning knobs, sliding knobs). If desired, the handset 550 also can include a visual display, such as a graphical user interface (GUI), and the handset controls 594 can also include one or more elements (e.g., a track ball and/or a joystick) to enter GUI commands.

The handset 550 combines display and control features that assist a user in monitoring and controlling operation of the remote viewing device 110 and in observing, evaluating and recording the results of an inspection performed using the remote viewing device. The handset 550 also typically provides electrical and optical communication as necessary between the various cables and replaceable probes that are used in the operation of the remote viewing device 110. Commonly assigned U.S. Pat. No. 5,373,317 to Salvati et al., the entirety of which is incorporated by reference herein, describes an embodiment of a unitary device, similar to the handset 550, that includes both a display module and a manually operated control module, and that performs interconnect functions between the cables and replaceable probes of a borescope.

Figure 2:
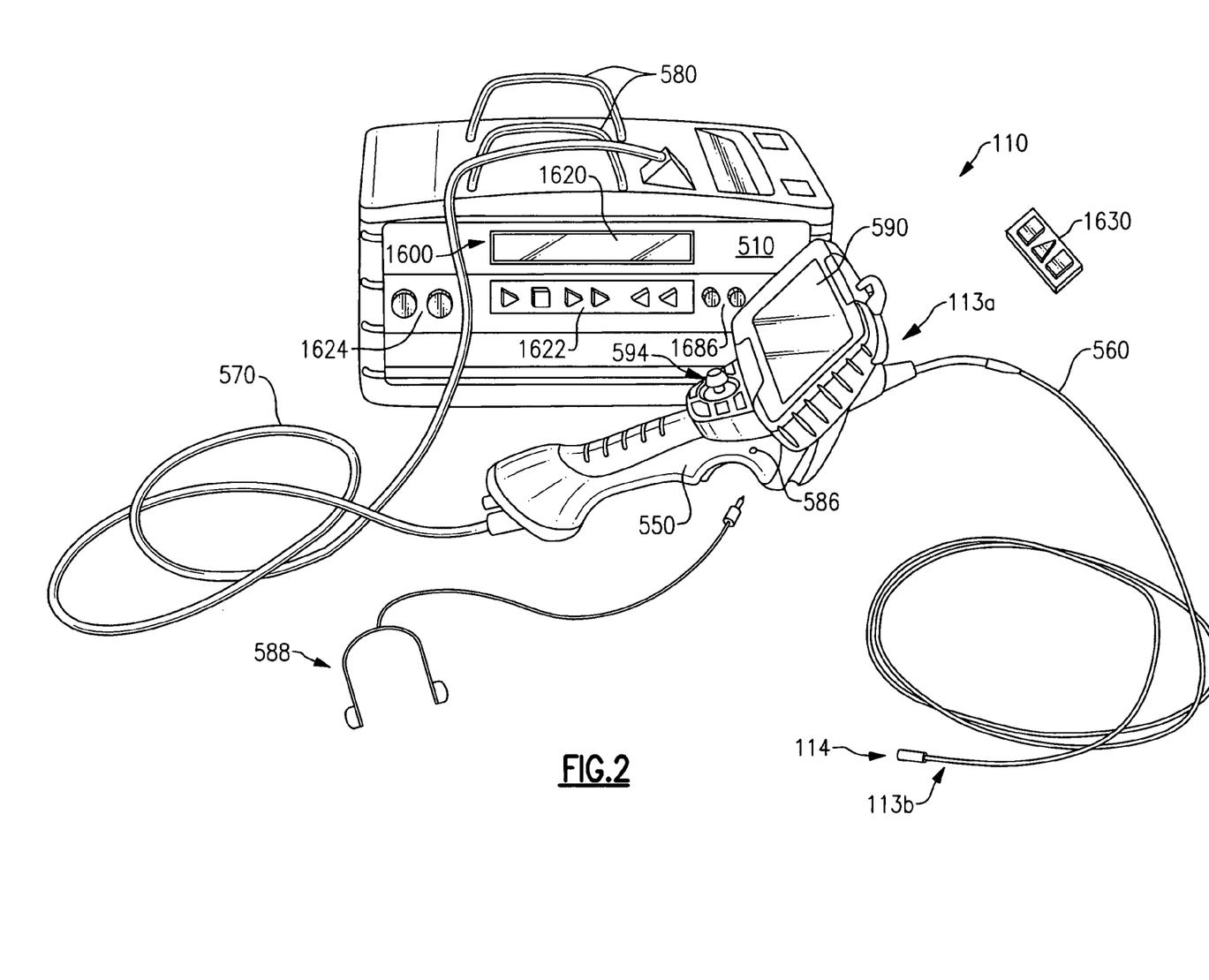
FIG. 2 illustrates the exemplary embodiment of FIG. 1 further including an exemplary audio output device.

FIG. 2 illustrates an exemplary embodiment similar to the exemplary embodiment depicted in FIG. 1, but that also includes an audio device 1600. In this exemplary embodiment, the audio device 1600 is implemented as a compact disk (CD) player/drive 1600. As shown, the compact disk drive 1600 is disposed within the base module 510 adjacent to a set of user interface controls 1622. If desired, however, a set of user interface controls 1622 can be disposed elsewhere within the body portion of the remote viewing device 110, such as within the handset 550.

The user interface controls 1622 provide typical CD player control functionality that enables a user to selectively control the output of the one or more audio tracks recorded onto a CD (not shown) that is loaded into the CD drive 1600. By way of non-limiting example, the user interface controls 1622 enable a user to play, pause, stop, skip forward, and/or skip backward among the one or more audio tracks recorded onto the CD loaded into the CD drive 1600.

It should be noted that the "body" of the remote viewing device 110, as referred to herein, denotes the one or more portions of the remote viewing device 110 other than a tube, wire or cord. Thus, according to this definition, the body portion of the device includes the base module 510 and the handset 550 but excludes the insertion tube 560 as well as the umbilical cord 570 and power cord portions of the device 110. In an exemplary embodiment, the remote viewing device 110 includes a separate display monitor (not shown) that is connected to the base module 510 (e.g., by wire line). In accordance with such an embodiment, the body portion of the remote viewing device 110 generally, but not necessarily, would include a separate display monitor.

In an exemplary embodiment that includes an audio output or communication device 1600, a user headset 588 includes at least one embedded speaker and receives audio information communicated from the audio output device 1600. The presence of the headset is useful for various reasons, including that it allows a user to listen to audio information without disturbing others who may be in proximity. The headset can be connected to the body of the remote viewing device 110 in various ways, including, by way of non-limiting example, by a wire line connection through use of an audio input connector. In accordance with such an embodiment, the headset 588 can be wire line connected to the remote viewing device 110 via an audio input connector 586 that resides within the headset 588 or via an audio input connector residing among an audio input/output connector pair 1686 that is disposed within the base module 510. The headset 588 can include a microphone (not shown) and can be in communication with the remote viewing device 110 via a wireless connection, which complies with one or more of various wireless communication standards, including but not limited to Bluetooth standards and/or the IrDA® (Infrared Data Association) standard. Such an embodiment can be beneficial if, for example, the remote viewing device 110 is being used in an environment where ambient noise can be distracting.

In accordance with an exemplary embodiment in which the audio output device 1600 is a CD player/drive, a user of the remote viewing device 110, if desired, can generate and listen to audio information recorded onto a CD media via the CD player 1600 operating as an audio output device 1600 disposed within the remote viewing device 110. The user can employ the audio generation functionality of the audio output device 1660 if, for example, the user wishes to memorialize observations the user makes during the inspection process. In an exemplary variation of such an embodiment, the CD player 1600 can extract recorded audio information from the CD and transmit the recorded audio information to the user of the device 110 via the headset 588. If desired, the user also can employ the audio extraction functionality of the audio output device 1600, such as for entertainment purposes (e.g., to listen to music or a book on CD) and/or for instructional purposes, as described in greater detail herein (e.g., to receive instructions on how to operate the remote viewing device 110 and/or what areas to inspect during the inspection process). It should be noted that the user can employ the audio extraction functionality to listen to audio information either while operating the remote viewing device 110 and/or while performing other actions between periods of operating the device.

In use, the user can wear the headset 588 around or over the user's ears, while the headset 588 receives audio information from the audio output device 1600. It should be noted, however, that the headset 588 can be in the form of so-called "ear buds" that are placed within—rather than around or over—the user's ears. In an exemplary embodiment, the headset 588 is wire line connected to the body of the device 110, such as connected to either the base module 510 or the handset 550.

At least one speaker 1624 (shown as two speakers) can be disposed within a body portion of the remote viewing device 110, such as within the base module 510 or the handset 550. The at least one speaker 1624 can be present in addition to or in lieu of the headset 588, wherein the presence of the speaker(s) 1624 is useful because it enables a user to employ the audio extraction functionality of the remote viewing device 110 while being able to contemporaneously hear what could sometime be important extraneous noise (e.g., shouted instructions and/or warnings, alarms, announcements over a public address system) more easily than if the user was wearing the headset. The at least one speaker 1624 can be implemented, by way of non-limiting example, as a plurality of stereo and/or surround sound speakers.

Also by way of non-limiting example, the at least one speaker 1624 can be disposed within the base module 510 and can be in communication with the audio output device (e.g., CD player) 1600. In an exemplary variation of such an embodiment, the at least one speaker 1624 unconditionally broadcasts audio information transmitted by the CD player 1600 through the atmosphere and to the user of the device 110, whether or not the wire line connectable headset 588 is physically connected to the remote viewing device 110. In another exemplary variation of such an embodiment, the at least one speaker 1624 broadcasts audio information through the atmosphere and to the user of the remote viewing device 10 when the wire line connectable headset 588 is not connected to the remote viewing device. In accordance with such a variation, the at least one speaker 1624 does not broadcast audio information when the wire line connectable headset 588 is connected to the body of the device 110, such as when the headset is connected to either the base module 510 or the handset 550.

In accordance with another exemplary embodiment, the headset 588 communicates with the audio output device 1600 via a wireless connection. This can occur, but way of non-limiting example, wherein a wireless transmitter (not shown) resides within the body of the device 110 and transmits wireless signals to a wireless receiver (not shown) residing within the head set 588. Such a wireless connection can comply with one or more of various wireless communication standards, including but not limited to Bluetooth standards and/or the IrDA® (Infrared Data Association) standard.

If desired, a set of controls like the set of user interface controls 1622 disposed within the base module 510 can be disposed within the handset 550 (e.g., and as is currently preferred, among the handset controls 594). In accordance with such an embodiment, the handset controls 594 communicate with the audio output device via a wireless or a wire line connection. The wire line type of connection can be implemented, by way of non-limiting example, via the umbilical cord 570, whereas the wireless connection complies with one or more of various wireless communication standards, including but not limited to Bluetooth standards and/or the IrDA® (Infrared Data Association) standard.

Also if desired, the audio output device user interface controls 594 disposed within the handset 550 can electronically interface with a wireless transmitter (not shown) that is also disposed within the handset. In accordance with such an embodiment, the wireless transmitter communicates user commands entered via the audio output device user interface controls 594 disposed within the handset 550 to a wireless receiver (not shown) that is disposed within the base module 510. The wireless receiver interfaces with the audio output device 1600 to enable a user to control the operation of the audio output device using the handset 550, e.g., via wireless communication. It is currently preferred, but not required, for the wireless transmitter and receiver conform to the Bluetooth trade association standard.

In accordance with yet another exemplary embodiment, a set of controls like the set of user interface controls 1622 disposed within the base module 510 also can be disposed within a remote control device 1630. The remote control device 1630 can have a wire line or, as is currently preferred, a wireless connection to the audio output device 1600. If desired, the remote control device 1630 can be used as an optional and additional means for controlling the audio output device (e.g., CD player) 1600. The remote control device can take various forms, including, by way of non-limiting example, as a wireless battery powered infrared (IR) device. In accordance with such an embodiment, the base module 510 includes an infrared (IR) communication port for receiving commands from the IR remote control device 1630. If the base module 510 includes an IR communication port, it is currently preferred, but not required, for the IR communication port to be compatible with the IrDA® (Infrared Data Association) communication standard.

Whether disposed within the base module 510, the handset 550 or the remote control device 1630, the set of controls (like 1622) generally enables a user to selectively control the output of audio information from the audio output device 1600. By way of non-limiting example, the set of controls (like 1622) enable a user to play, pause, stop, skip forward, and/or skip backward among one or more audio tracks recorded onto a CD loaded into the audio output device (e.g., CD drive) 1600.

When present, the audio output device 1600 can configured, if desired, to process one or more various types of portable media, including various types of disk media, in order to output audio information therefrom. By way of non-limiting example, the audio output device 1600 can be configured to function as a disk drive (i.e., as a media player) that can process (i.e., that can play) read only (e.g., CD-ROM), write once (e.g., CD-R) and/or read/write (e.g., CD-RW) compact disk media and/or digital video disk (DVD) media. The term "DVD disk media," as used herein, is synonymous with the term "DVD audio."

If desired, the audio output device 1600 can process media having digital data recorded thereon. By way of non-limiting example, there are currently available commercially CD drives, including but not limited to those sold by AIWA, that can process both CDs purchased from retail music stores storing encoded audio information (e.g., in .WAV format) and those with recoded digitally encoded information (e.g., in .MP3 format). It is understood, however, that the audio output device 1600 also can be adapted to process other types of digital formats, including but not limited data in .wma, .OGG, and .VQF audio-formats.

Also if desired, the audio output device 1600 can function as a recorder and be configured to write (i.e., "burn") disk media, such as a CD or DVD disk. In accordance wit such an embodiment, and by way of non-limiting example, audio from a user of the device can be captured (e.g., via a microphone (not shown)) and can be recorded onto media or into memory, such as flash or RAM memory. Alternatively, and also by way of non-limiting example, the audio output device 1600 can be configured to process (i.e., play) or to write mini disks, which are disks that have similar capabilities to but comparatively substantially smaller diameters than compact disks.

Still also if desired, the audio out put device 1600 can be configured to output video media in lieu of or in addition to audio media. In accordance with such an embodiment, and by way of non-limiting example, the outputted video can be displayed on the display 590, or, instead, a video recording device (not shown) can record video captured via the viewing head 114 and recorded onto media, such as onto tape or disk, or that is recorded into memory, such as flash or RAM memory, wherein the memory can be configured to be portable, such as portable flash memory that communicates through a USB port.

If yet also desired, the audio output device 1600 can be configured to process other types of portable media and can function as a tape player or a memory card reading device. If configured as a tape player, it is currently preferred, but not required, for the audio output device 1600 to be a tape cassette player. If configured as a memory card reading device, it is currently preferred, but not required for the audio device 1600 to be compliant with Personal Computer Memory Card International Association (PCMCIA) standards. Also, the memory card reading device can accommodate a Compact Flash memory card, or an SD (Secure Digital) or SDIO (Secure Digital Input/Output) memory card. Alternatively, the audio output device 1600 can be configured to process information recorded onto magnetic disks, such as portable magnetic disk media.

The aforementioned types of media can function as analog or digital memory and can store audio information that is encoded into various types of formats, including but not limited to those compliant with .WAV and .MP3 standards. As is known to those of ordinary skill in the electronic storage media arts, news media and formats for data storage are continually being devised, and any convenient, commercially available storage medium and corresponding read/write device that may become available in the future is likely to enhance the use in the remote video inspection system 110, especially if it provides any of a greater storage capacity, a higher access speed, a smaller size, and a lower cost per bit of stored information.

If desired, the audio output device 1600 can be configured to receive signals encoding audio information. By way of non-limiting example, the audio output device 1600 can include a receiver for AM and/or FM broadcast radio transmitted in analog or digital (e.g., HD radio®) format, and/or can include receiver for radio transmitted via a satellite (e.g., via a subscription service such as Sirius or XM radio).

Figure 3:
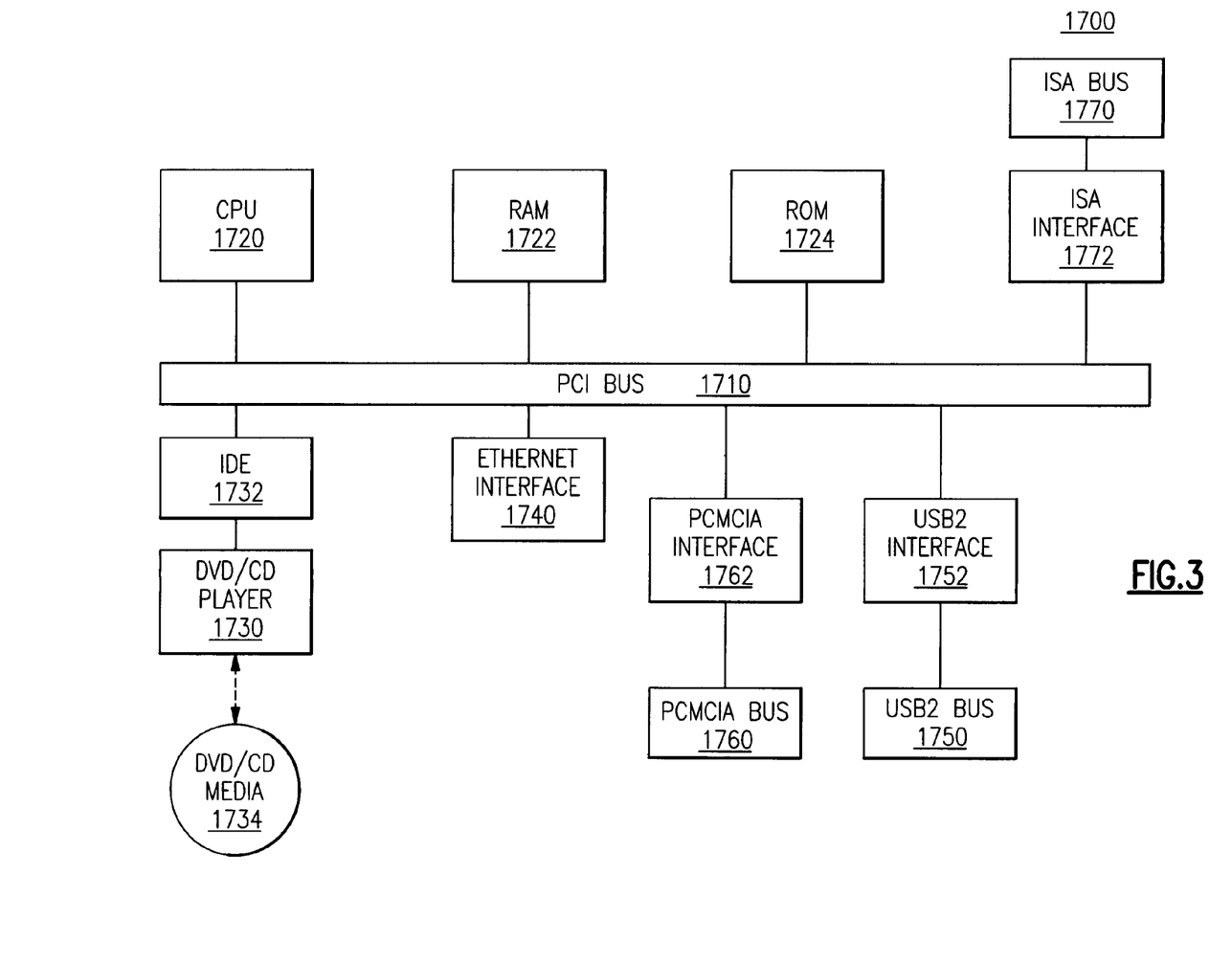
FIG. 3 is a block diagram illustrating an exemplary embodiment of a computation module configured to interoperate with an audio output device (such as that which is shown in FIG. 3) and other peripheral electronic components.

Referring now to FIG. 3, a block diagram is shown that illustrates an exemplary embodiment of a computation module 1700 configured to inter-operate with an audio output device 1600 and one or more other peripheral electronic components. As shown, and by way of non-limiting example, the audio output device is a DVD/CD media player 1730. It is currently preferred that the computation module 1700 comply with industry standards associated with Microsoft Windows compatible personal computers and that the computation module reside within the base module 510 of the remote viewing device 110. If instead desired, the computation module 1700 can comply with other industry computer standards or can be of a proprietary design.

As shown, and by way of non-limiting example, the computation module 1700 includes a central processing unit (CPU) 1720 and one or more other electronic components that are electronically connected to a PCI bus 1710, which functions as a main bus within the computation module 1700. The main bus 1710 attaches to and communicates with other bus types, including, but not limited to, the Universal Serial Bus—Version 2.0 (USB2) bus 1750, PCMCIA bus 1760 and the Industry Standard Architecture (ISA) bus 1770. The PCI bus (i.e., main bus) 1710 is electronically connected to a (CPU) 1720, to random access memory (RAM) 1722, to read only memory (ROM) 1724, and to an (IDE) controller 1732, which controls the DVD/CD media player 1730. The DVD/CD media player 1730 processes (i.e., plays) a DVD/CD disk media 1734 that is inserted into the player 1730 via a disk media input/output port 1620 (see FIG. 2).

If desired, the computation module 1700 can be configured to inter-operate with many other types of audio output devices 1600, including, but not limited to, those audio output devices previously identified and discussed herein. The PCI bus (i.e., main bus) 1710 also can be connected to an Ethernet communications network (e.g., via an Ethernet interface card 1740), to a PCMCIA bus 1760 (e.g., via a PCMCIA bus interface controller 1762), to a USB2 bus 1750 (e.g., via a USB2 bus interface controller) and/or to an ISA bus 1770 (e.g., via an ISA bus interface controller 1772). It is also understood that the audio output device 1600 can be connected to other bus types that, in turn, are connected to the main bus 1710 or that function as the main bus.

The computation module 1700 enables software executing on the CPU 1720 to control and monitor the operation of the audio output device 1600 and other peripheral hardware. The other peripheral hardware can include, but is not limited to interfaces to one or more types of data communication links that enable the base module 510 to receive and/or transmit digital data to and from a remote device, such as to and/or from a remote computer. By way of non-limiting example, wireless communications interface hardware can be connected to a USB 2.0 port or to the PCMCIA system bus slot. Optionally, available PCMCIA system bus slots can be utilized, by of non-limiting example, to accommodate USB 2.0, Ethernet, Firewire (IEEE 1394) and/or serial modem interface hardware. Also, available PCMCIA system bus slots can be utilized, by way of non-limiting example, to accommodate IEEE 802.11 (B, A, or G) and/or Bluetooth compliant wireless interface hardware.

It is currently preferred, but not required for the peripheral communication hardware, whether of a wire line or wireless type, to be utilized in order to provide communication to the communications medium commonly referred to as the "Internet." By way of non-limiting example, wireless interface hardware can provide a data communications link through which the base module 510 communicates with a wireless accessible connection to the Internet. Alternatively, and also by way of non-limiting example, an Ethernet card provides a data communications link through which the base module 510 communicates with an Ethernet accessible connection to the Internet. If instead desired, and also by way of non-limiting example, the base module 510 can communicate with the Internet via a serial modem connection to an Internet Service Provider (ISP) that provides a connection to the Internet.

The aforementioned types of data communication links enable the remote viewing device 110 to communicate with other remote devices, such as with a computer residing within a remote data processing facility, thus enabling audio information to be digitally encoded and communicated to the base module 510 from a remote computer. By way of non-limiting example, audio information encoded as .MP3 data can be communicated to the base module 510 from a remote computer and processed by an .MP3 player residing within the base module 510. In accordance with such an embodiment, at least a portion of the MP3 player is implemented as a software module executing via the CPU residing within the base module 510.

Figure 4:
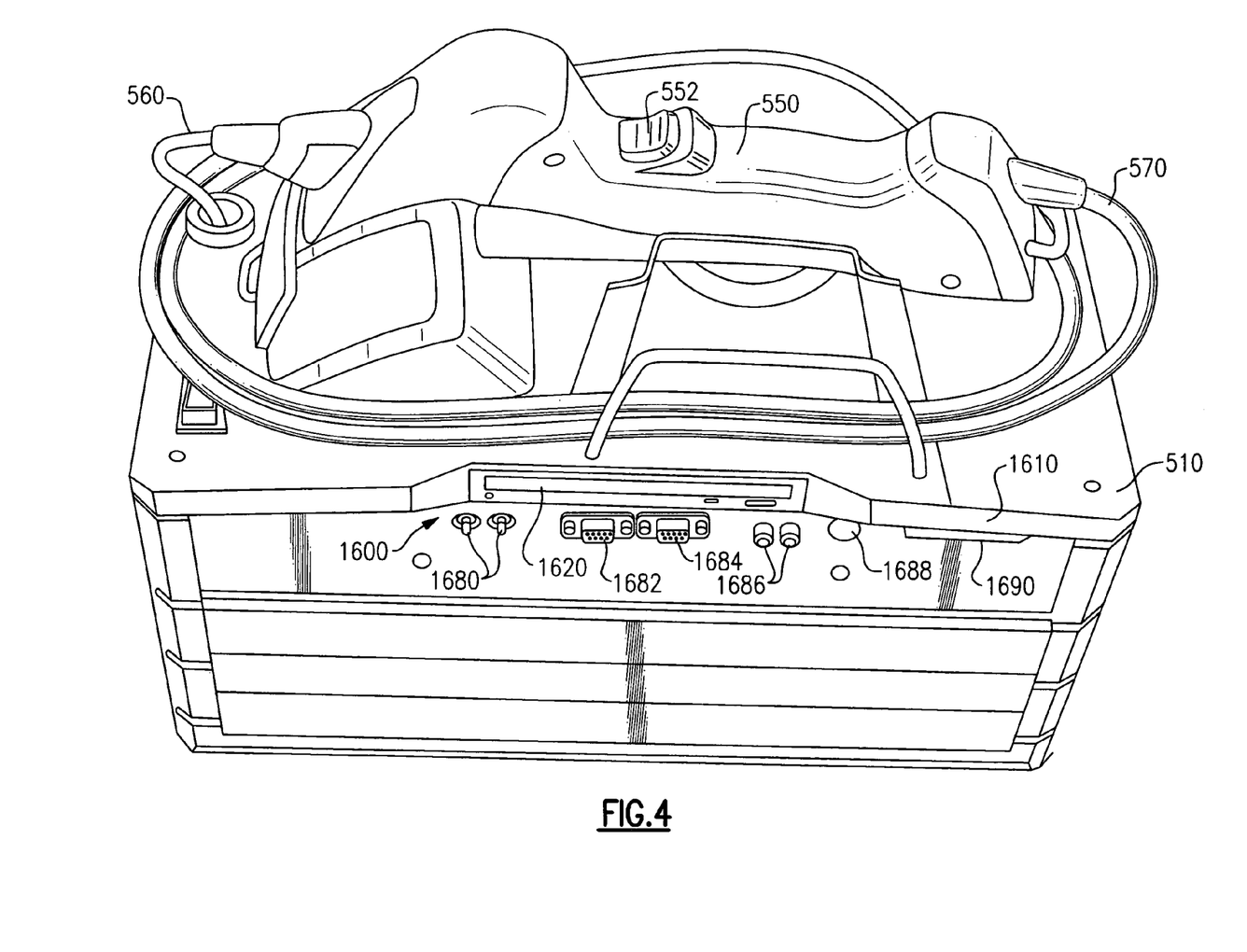
FIG. 4 illustrates the exemplary embodiment of FIG. 2 including various additional electronic components.

Referring now to FIG. 4, it illustrates an embodiment of the invention like that which is shown in FIG. 2, but also including additional components. For example, the base module 510 in FIG. 4 includes an aperture 1610 that can accept various types of electronic cards (e.g., PCMCIA, PC or Compact Flash cards), that can implement modem, memory, Ethernet, Firewire® and/or other types of functionality to support the operation of the computation module 1700, and/or that can accept SD (Secure Digital) or SDIO memory cards. Moreover, the handset 550 includes a trigger button 552, which, when actuated, can initiate one or more functions of the remote viewing device, such as the capture of image data. As shown, the trigger button 552 is located on the underside of the handset; however, it is understood that the trigger button instead can be located elsewhere on the handset or on another portion of the remote viewing device.

As shown in FIG. 4, a disk media input/output port 1620 resides within an opening of a DVD/CD player device 1600 and functions as a portion of the device 1600, wherein the disk input/output port provides access to hardware that processes various types of physical media including, but not limited to, CD-ROM disks (i.e., read-only optical storage disks), CD-R disks (i.e., write-once, read-many optical storage disks), CD-RW disks (i.e., rewriteable optical storage disks) and DVD disks. Also as shown, the base module 510 can include S-video input/output connectors 1680, a VGA (Visual Graphics Array) output connector 1682, a DVI (Digital Visual Input) output connector 1684, audio input/output connectors 1686, a USB (Universal Serial Bus) port 1688 and/or a power switch 1690. Moreover, a bus slot, whether it connects within a PCI, PCMCIA, ISA or other type of bus, can be used to connect hardware to the computation module 1700. Such hardware can function, by way of non-limiting example, to interface with one or more of the types of aforementioned external connectors or to add a variety of hardware and/or software functions or capabilities to the remote viewing device 110. In accordance with an exemplary embodiment, an electronic card reader can be connected via a bus slot to input information, including software, to the computation module 1700.

The variety of hardware and software functions of the remote viewing device 110 include, but are not limited to, the ability to receive and play (i.e., process) audio data, such as audio data encoded within .MP3 files or within other audio encoding formats (e.g., .wma, .wav, .qt, .ra, .ram, .au, .aif, .aif). Audio data can represent audio entertainment (e.g., music, books on CD) and/or information relating to the inspection process (e.g., instruction to the user relating to usage of the remote viewing device and/or its features, instruction or guidance relating to what areas are to be inspected with the remote viewing device, recorded text from usage and/or maintenance manuals, vocalization of pass/fail criteria, etc.). Audio data can be accessed from on or more database and can be added to the remote viewing device 110 at the time of its manufacture or, if instead desired, added at a later time (e.g., by a user in the field).

Figure 5:
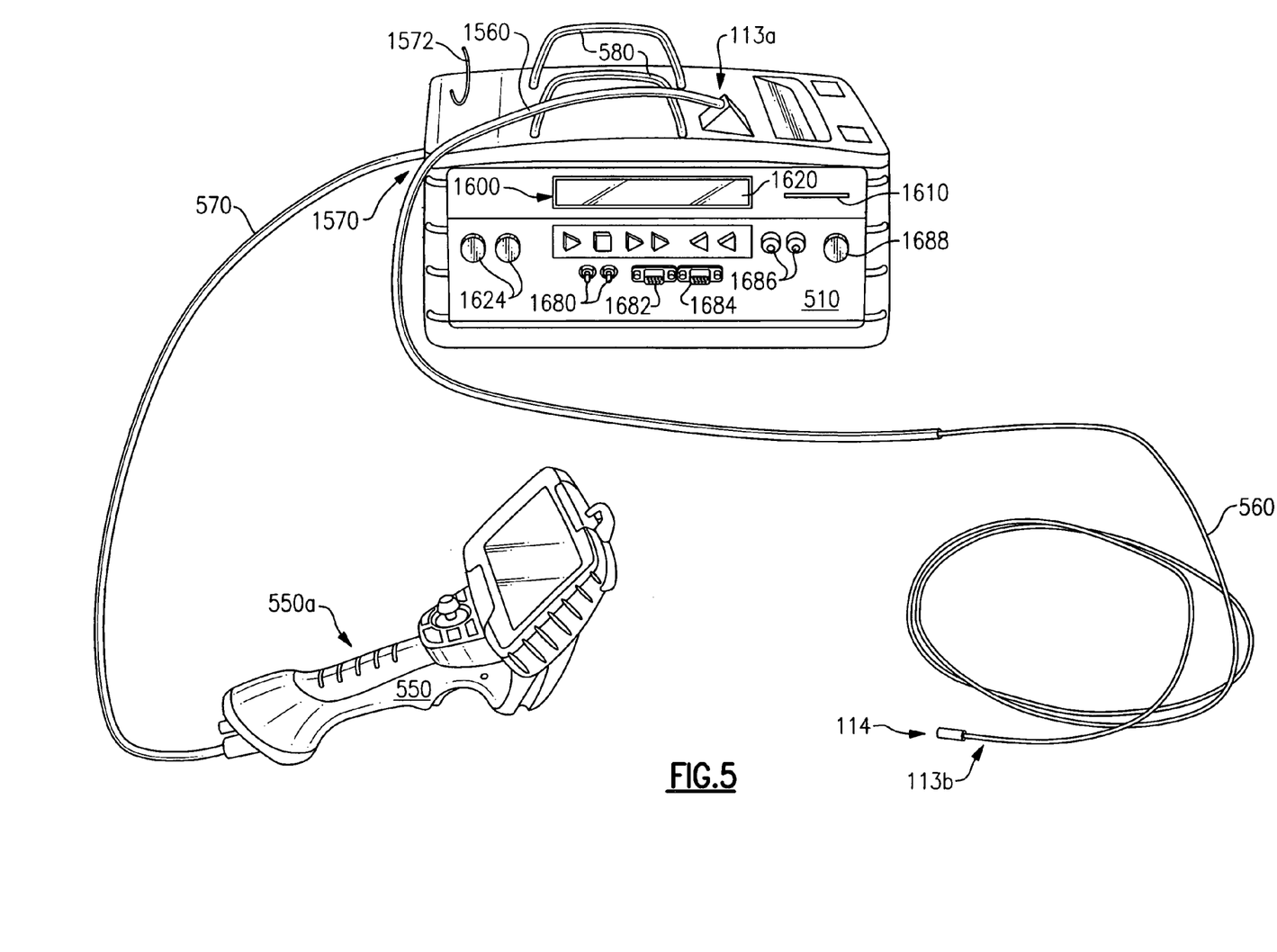
FIG. 5 illustrates an exemplary embodiment of a remote viewing device that includes a handset control module and an insertion tube that are connected to a base unit but not to each other.

Referring now to FIG. 5, it illustrates an embodiment of the invention, which, like that which is shown in FIGS. 2 and 4, includes a handset control module 550 and an insertion tube 560 that are connected to a base unit 510 rather than to each other. As shown, and by way of non-limiting example, the base module 510 has a first connection 1570 to a handset 550 via an umbilical cord 570 and a second connection 1560 to an insertion tube 560 having a viewing head assembly 114 attached to its distal end 113b. The base module 510 is electronically connected to the handset 550 via the umbilical cord 570 and optically and electronically connected to the viewing head assembly 114. If desired, such an embodiment can include some or all of the structural and functional attributes described in association with the embodiments depicted and described with respect to FIGS. 1-4.

In a variation of such an embodiment, the control module 550 can be attached to or included within the base module 510, and thus not require connection via the umbilical cord 570 as shown. Optionally, the control module 550 can be electrically connected to the base module 510 via the umbilical cord 570 and can be further mechanically and removably attached to the base module 510 via a third connection 1572, which is configured to receive and frictional attach to a hand graspable portion 550a of the control module 550.

Figure 6:
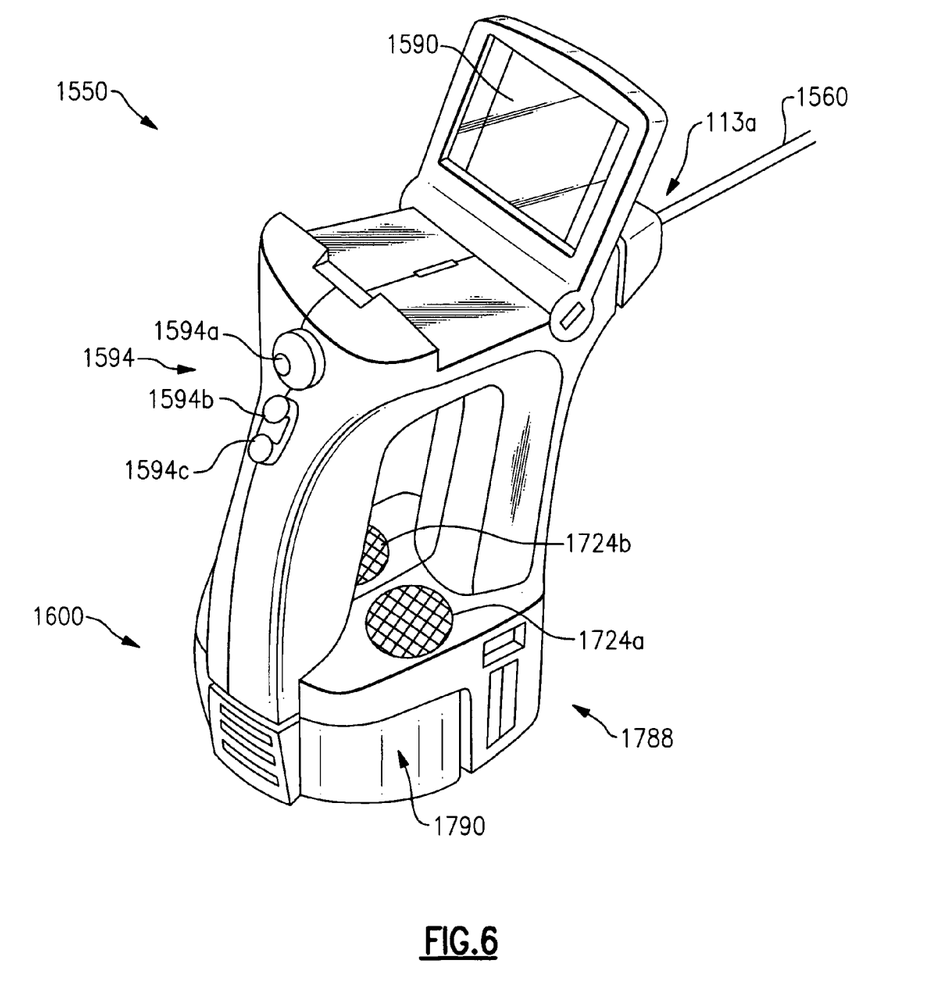
FIG. 6 illustrates an exemplary embodiment of a remote viewing device that includes a handset control module that operates independently of a base unit.

Referring now to FIG. 6, it illustrates an embodiment of a remote viewing device that includes a handset control module (handset) 1550 that operates independently of a base unit. As depicted and by way of non-limiting example, the handset 1550 is connected to an insertion tube 1560 having a viewing head assembly (not shown) attached to its distal end (not shown). The handset 1550 can be powered by a suitable powering element (e.g., a re-chargeable battery) 1790 located within the base (i.e., bottom) of the handset 1550.

As described and depicted in association with the various embodiments of FIGS. 1-5, the handset 1550 in FIG. 6 also functions as a control module and is electronically and optically connected to the viewing head assembly via the insertion tube 1560. A continuous video image is captured by the viewing head assembly and is displayed via the handset display 1590. The handset 1550 also receives command input from a user via the handset controls 1594 in order to perform various remote insertion tube device 1560 operations. A handset control circuit (not shown) that is disposed within the handset 1550 interprets commands entered via handset controls 1594 so that the distal end (not shown) of insertion tube 1560 is moved into a desired orientation.

The handset controls 1594 can include various combinations of actuation devices such as one or more buttons, knobs (e.g., turning knobs and/or sliding knobs), track balls, an/or joy sticks. As shown in FIG. 6, and by way of non-limiting example, the handset controls 1594 include a joystick 1594a, and buttons 1594b, 1594c.

The handset 1550 combines display and control features that are useful for a user to monitor and control the operation of the remote viewing device 110 and to observe, evaluate and record the results of an inspection using the device. To that end, the handset 1550 includes a visual display 1590, which optionally provides a graphical user interface (GUI). The handset 550 also typically, but not necessarily, provides electrical and optical communication as necessary between the various cables and replaceable probes that are used in the operation of the remote viewing device 114.

If desired, and as shown in the FIG. 6 exemplary embodiment, an audio output device 1600 can be embedded inside of the handset 1550 and is effective to output audio information via one or more speakers 1724a, 1724b. Various electronic input/output ports 1788 including, but not limited to, one or more ports types such as a USB 2.0 or serial port, enable transfer of audio information to digital memory that is also embedded within the handset 1550.

By way of non-limiting example, the handset 1550 can be configured to process audio information, such as an MP3 or other format, that is stored within its digital memory, wherein the audio information can be communicated to the handset 1550 via one of the one or more input/output ports 1788. The audio input/output ports 1788 also enable the remote viewing device 1550 to communicate with other remote devices, such as with a computer residing within a remote data processing facility. Thus, audio information can be digitally encoded and communicated to the handset 1550 from a remote computer.

By way of non-limiting example, audio information encoded as .MP3 data can be communicated to the handset 1550 from a remote computer and processed by an audio output device, implemented, e.g., as a software-based .MP3 player, residing within the handset 1550. In accordance with such an embodiment, at least a portion of the MP3 player is implemented as a software module executing via the CPU residing within the base module 510.

The audio capabilities described in one or more of the above embodiments also can be employed to facilitate usage of a remote viewing device. For example, because the audio capabilities provide non-visual output to a user of the remote viewing device in the form of audio information, such capabilities can be beneficially combined with or substituted for one or more visual-based features of a remote viewing device. By receiving information in both visual and non-visual formats, a user of the remote viewing device is less likely to make mistakes or to somehow miss information. Moreover, a user can opt to ignore or focus comparatively less upon the visual-based information in favor of the non-visual information, thus enabling the user to direct his or her visual attention on other tasks, a useful feature in hazardous operating environments. If instead desired, a user can receive information solely in a non-visual form, e.g., via audio output, without accompanying visual-based information. This can be beneficial under various circumstances, such as if a user is unable to position himself or herself to view visual-based information, or if the user wants to reduce the power consumption of the remote viewing device.

An exemplary visual-based system for use with a remote viewing device is depicted and described in commonly assigned U.S. Provisional Patent Application Ser. No. 60/786,829 ("the '829 application") entitled "INDUSTRIAL EQUIPMENT ARTICLE INSPECTION SYSTEM," the entirety of which is incorporated by reference herein. The '829 application describes a visual-based, menu-driven system that includes various features to facilitate usage of a remote viewing device.

In accordance with various embodiments depicted and described in the '829 application, a remote viewing device displays (e.g., on a hand set display and/or a monitor display similar to those depicted and described herein) visual information to guide a user regarding how to use a remote viewing device to perform a visual inspection process and/or to provide the user with visual-based feedback regarding the ongoing inspection process. Such feedback can occur, e.g., at the outset of an inspection step, during an inspection step, when a step in the inspection process has been completed, when a problem has been encountered during the inspection process, etc. The visual-based guidance and/or feedback information of the '829 application can be presented, e.g., in a menu-driven format, whereby a user can maneuver through various menu options and screens by pressing or otherwise actuating handset buttons or knobs similar to those depicted and described herein, and/or by touching the screen on which the menu is displayed.

In accordance with an exemplary embodiment in which the non-visual audio capabilities described herein are combined with a visual-based guidance and feedback system such as that of the '829 application, the non-visual and visual capabilities of the combined system can be adapted to be simultaneously operational such that a user of the remote viewing device receives both visual and non-visual information, or non-simultaneously operational whereby a user receives one of, but not both, visual and non-visual information. When the visual and non-visual capabilities are both operational, the user can elect to discontinue the output of either or both the visual and non-visual information. This can be accomplished, by way not non-limiting example, via a voice command, via a menu screen selection and/or via positioning of a user-actuatable switch, button, knob or other like actuation means. If a user wishes to again receive the discontinued visual or non-visual information, the user can reverse the step(s) take to discontinue such information.

Audio information, when not discontinued, can be supplied at predetermined intervals to a user of the remote viewing device. Such predetermined intervals can be, e.g., when the device is low on power, or when the memory capabilities of the device are at or near capacity. Additionally, audio information can be selectively supplied to the user while and/or after the user takes certain predetermined actions. For example, the user can receive audio information after the user has caused the remote viewing device to record an image. This beneficially enables a user to receive non-visual confirmation of the image having been memorized, thus allowing the user to focus his or her attention entirely or partially on other visual-based tasks at that time.

In a similar vein, the predetermined actions that trigger non-visual information being selectively supplied to a user can be tied to the user browsing and/or selecting from a menu screen, as both occur in furtherance of the system depicted and described in the '829 application. For example, a user can browse a menu screen using buttons or knobs on the handset of the remote viewing device and, upon locating a desired menu option, can select the choice by pressing a certain button of the handset. As each menu option is highlighted during the browsing process, audio information can be provided to the user so as to non-visually inform the user that a particular menu choice is highlighted and can be selected. Once the menu option is selected, the user receives audio confirmation of the selection.

By providing a user with audio information as such, the user need not pay complete or even partial visual attention to the menu screen during the menu browsing and/or selection processes. Instead, the user can receive non-visual, audio information sufficient to make menu choices and to learn if his or her menu selections were made as intended. Moreover, a user—especially one familiar with the remote viewing device—may tend to be able to operate the handset by touch alone (i.e., without looking at the handset) through familiarity and/or through use of "hot" keys. Thus, the non-visual information provided in the form of audio output can enable a user to operate a remote viewing device via a menu-driven system while partially or even entirely focusing his or her visual attention elsewhere. This provides valuable benefits heretofore unavailable to a user of a remote viewing device. For one, it enables a user to continually focus his or her attention on the space or area that is being inspected by the remote viewing device, rather than having to draw his or visual attention away from and then back to the space or area in order to view menu options and/or to make menu selections.

The benefits of providing non-visual guidance and/or feedback to a user of a remote viewing device are not limited to enabling the user to focus his or her visual attention on other tasks in furtherance of making menu selections. Another such benefit relates to more quickly and reliably informing a user that he or she has made an error, such as an incorrect or unintended menu selection. In particular, when a user hears audio confirmation of a menu selection, he or she instantly can determine if the selection was incorrect or unintended. That, in turn, enables the user to halt the visual inspection process and take the appropriate steps to negate the selection or to perform other corrective action(s). If, instead, there was no audio confirmation of the menu selection, then the user might not deduce that he or she had made an incorrect or unintended selection until well after the user has wasted valuable time and resources. Plus, depending on the gravity of the error, the user might be forced to retrace his or her steps in order to restart the visual inspection process at or near the exact time or place when the error was made. Not only will that also waste valuable time and resources, but it could frustrate the user, perhaps to an extent that he or she will not perform the visual inspection process as optimally as he or she would have if the error could have been realized and corrected more quickly.

It is understood that certain circumstances may exist whereby it is not necessary or not as beneficial for a user of a remote viewing device to receive guidance and/or feedback information via audio output. For example, the user may be familiar with the operation of the remote viewing device to an extent whereby he or she not longer would benefit from receiving such audio information, or perhaps there may be gaps in time between when a user would need to browse or select from menu options. Under such circumstances, and any others, the user can opt to discontinue the audio output of the remote viewing remote viewing device as discussed above, or, instead, can cause the remote viewing device to provide audio output in the form of audio entertainment in lieu of audio guidance and/or feedback information. This can occur as is generally known in the art, e.g., by actuating a switch on the handset and/or body portion of the remote viewing device from an "audio information" setting to an "audio entertainment setting." Alternatively, the user can activate a portable media device in communication with the audio output device so as to cause audio output to be in the form of audio entertainment rather than in the form of audio information.

Although various embodiments have been described herein, it is not intended that such embodiments be regarded as limiting the scope of the disclosure, except as and to the extent that they are included in the following claims—that is, the foregoing description is merely illustrative, and it should be understood that variations and modifications can be effected without departing from the scope or spirit of the various embodiments as set forth in the following claims. Moreover, any document(s) mentioned herein are incorporated by reference in its/their entirety, as are any other documents that are referenced within such document(s).

I claim:

1. A method of communicating audio information to a user of a remote viewing device, said method comprising the steps of:
   providing a remote viewing device comprising:
   an insertion tube having a proximal and a distal end;
   a control module disposed at said proximal end of said insertion tube, said control module providing at least a first portion of a user interface to a user of the remote viewing device;
   a viewing head disposed at said distal end of said insertion tube, said viewing head inputs and communicates image information to said control module;
   at least one speaker disposed at said proximal end of said insertion tube; and
   at least one audio output device disposed at said proximal end of said insertion tube in communication with said at least one speaker-configured to communicate audio information to a user of said remote viewing device;
   providing audio information to said at least one audio output device;
   processing said audio information with at least one audio output device; and communicating said audio information to said user from said audio output device through said speaker, wherein said audio information is selected from the group consisting of audio entertainment information, audio guidance information, audio training information, audio feedback information, audio menu-driven inspection information, and audio error notification information.

2. The method of claim 1, wherein said remote viewing device further comprises:
   a base module configured to relay power to at least one other portion of said remote viewing device.

3. The method of claim 1, wherein said audio information is processed from portable media.

4. The method of claim 3, wherein each of said at least one audio output device is selected from the group consisting: of a disk player device and a tape player device.

5. The method of claim 4, wherein said disk player device is selected from the group consisting of:
   a compact disk (CD) player device, a digital video disk (DVD) player device and a mini disk player device.

6. The method of claim 4, wherein said tape player device is selected from the group consisting of:
   a cassette tape player device and a videotape player device.

7. The method of claim 1, wherein said remote viewing device includes digital memory and wherein said at least one audio output device processes audio information stored within said digital memory.

8. The method of claim 7, wherein said remote viewing device includes a data communications port, and wherein said method further comprises the step of:
   receiving, via said data communications port, said audio information stored within said digital memory.

9. The method of claim 8, wherein said data communications port provides a wireless connection with another computing device.

10. The method of claim 1, wherein said at least one speaker is in communication with said at least one audio output device via a connection selected from the group consisting of:
    a wire line connection and wireless connection.

11. The method of claim 1, wherein said at least one speaker is a plurality of speakers, and wherein the plurality of speakers are selected from the group consisting of:
    stereo speakers and surround sound speakers.

12. The method of claim 1, wherein said at least one speaker is disposed within a body portion of said remote viewing device.

13. The method of claim 1, wherein said at least one speaker is disposed outside of said remote viewing device.

14. The method of claim 13, wherein said at least one speaker is disposed within a headset in communication with said at least one audio output device.

15. The method of claim 1, wherein said at least one audio output device includes at least one radio receiver.

16. The method of claim 15, wherein said at least one radio receiver is selected from the group consisting of:
    a broadcast radio receiver, a satellite radio receiver, and a high definition radio receiver.

17. The method of claim 1, wherein the remote viewing device includes a user interface and wherein said method further comprises the step of:
    controlling said at least one audio output device via said user interface.

18. The method of claim 17, wherein said user interface employs a wireless or wire line connection with said audio output device.

19. The method of claim 17, wherein the user interface is within a body portion of said remote viewing device.

20. The method of claim 17, wherein said user interface resides within said control module.

21. The method of claim 17, wherein said user interface resides within a remote control device.

22. The method of claim 1, wherein said audio menu-driven inspection information is communicated to said user upon said user taking at least one action selected from the group consisting of: highlighting a menu option, browsing within menu options, and selecting a menu option.

23. An inspection device, comprising:
    an insertion tube;
    a control module disposed at a proximal end of said insertion tube;
    a viewing head in electrical and optical communication with said control module through said insertion tube;

at least one speaker disposed at said proximal end of said insertion tube; and at least one audio output device disposed at said proximal end of said insertion tube in communication with said at least one speaker configured to communicate audio information to a user of the inspection device, wherein said audio information is selected from the group consisting of audio guidance information, audio training information, audio menu-driven inspection information, audio error notification information, audio feedback information and audio entertainment information.

\* \* \* \* \*